United States Patent [19]

Soukup

[11] Patent Number: 4,534,366
[45] Date of Patent: Aug. 13, 1985

[54] CARBON FIBER PACING ELECTRODE

[76] Inventor: Thomas M. Soukup, 38233 Hendon Dr., Palmdale, Calif. 93550

[21] Appl. No.: 519,957

[22] Filed: Aug. 3, 1983

[51] Int. Cl.³ .............................................. A61N 1/04
[52] U.S. Cl. ................................. 128/786; 128/419 P
[58] Field of Search ............................... 128/784–786, 128/419 P, 642, 640

[56] References Cited

U.S. PATENT DOCUMENTS

| 3,749,101 | 7/1973 | Williamson | 128/419 P |
| 4,102,331 | 7/1978 | Grayzel et al. | 128/640 |
| 4,156,429 | 5/1979 | Amundson | 128/419 P |

FOREIGN PATENT DOCUMENTS

| 2446001 | 9/1980 | France | 128/786 |
| 1219017 | 1/1971 | United Kingdom | 128/419 P |

Primary Examiner—Lee S. Cohen
Attorney, Agent, or Firm—Robert R. Meads; Bryant R. Gold

[57] ABSTRACT

An improved electrode tip (16) is disclosed which utilizes a plurality of carbon fibers (30) to form a portion of the electrode tip. These carbon fibers (30) are utilized to sense electrical activity within the user's heart, and in at least one embodiment to provide stimulation pulses to the heart. The fibers are chosen to have a cross-sectional diameter of less than 15 micrometers. These fibers form a limited porosity surface and allow a certain amount of tissue ingrowth, thereby providing passive electrode fixation. A body portion (24) of the electrode tip (16) forms an annular lip (32) which provides a surface for conducting stimulation pulses to the heart. Thus, a relatively small area is provided by the annular lip (32) for conduction of the stimulation pulses, thereby providing a high current density and less resistance. A larger surface area and a higher resistance is provided by the carbon fiber ends (44) for sensing electrical activity in the heart. In a still further embodiment of the invention, a porous retaining mesh (68) is located over a carbon fiber tip (66) for providing a more positive fixation by heart tissue ingrowth. The carbon fibers 30 are compressed to form a fiber compress in which the fibers form at least 85 percent of the compress volume.

20 Claims, 7 Drawing Figures

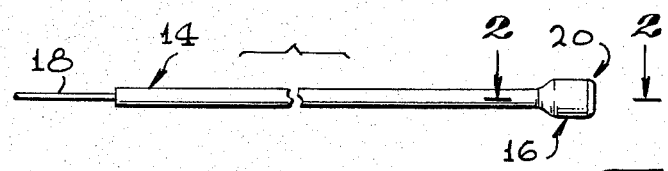
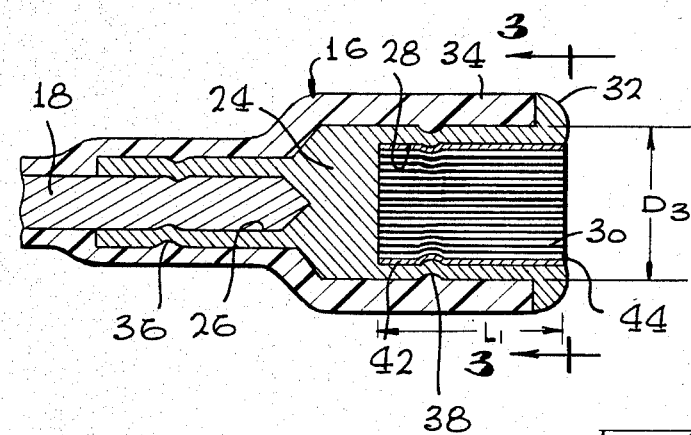
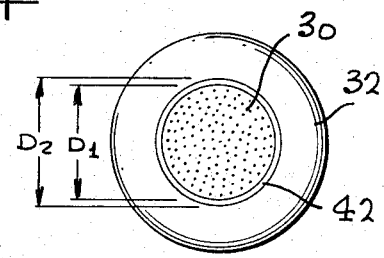
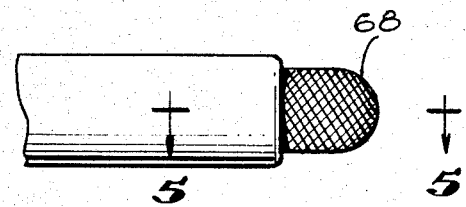
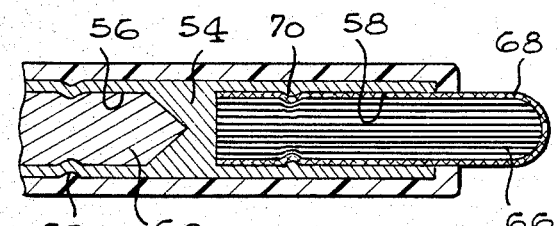
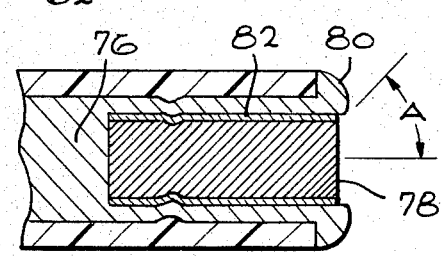

4,534,366

CARBON FIBER PACING ELECTRODE

TECHNICAL FIELD

The invention relates to an improved electrode tip for endocardial pacing leads that provide electrical continuity between the electrode tip located within a user's heart and an electrical stimulation device such as a heart pacemaker located external to the user's heart.

BACKGROUND ART

Leads and their associated electrodes or electrode tips originally used with asynchronous heart pacemakers were primarily designed to provide a low pacing threshold for continuous pulses that are generated at a predetermined rate regardless of any natural or unnatural heart activity. The next generation of cardiac pacemakers began with development of the demand pacemaker. With this type of pacemaker, the electrode served a dual purpose. It not only provided the pacing pulse to the heart, it was also used to electrically sense intrinsic heart activity for the purpose of suppressing a pacing pulse whenever a natural heartbeat occurred within a predetermined time period after the last natural heartbeat or pacing pulse. Similarly, development of the synchronous pacemaker required a pacing pulse to be provided either in the absence of a natural heartbeat, or in synchronism with the occurrence of a natural heartbeat whenever it occurred within a predetermined time period after the last pacing pulse. The electrode utilized with a synchronous pacemaker also served a dual function of providing a pacing pulse and electrically sensing the natural heartbeat. Subsequent heart pacemakers have become increasingly complex, and have numerous additional modes of operation which are selectable by a doctor according to a patient's physiologic needs. However, these increasingly complex pacemakers continue to utilize electrodes which serve the dual function of providing the pacing pulse and also sensing heart activity.

The requirements for an optimum pacing electrode and an optimum sensing electrode are sometimes conflicting. For example, an optimum pacing electrode would have a very small surface area exposed to the heart tissue in order to achieve a low pacing threshold and a high current density. However, a sensing electrode requires a large surface area in order to detect a relatively low level electrical signal indicating natural heartbeat activity. Prior art electrodes have attempted to balance these two requirements by sensing and pacing through the same exposed electrode surface, thus compromising the requirement of a small surface area for attaining a low pacing threshold and a large surface for detecting relatively weak electrical signals. Porous tip electrodes utilizing a platinum mesh have been developed such as that disclosed in U.S. Pat. No. 4,156,429. However, this type of prior art electrode utilizes a filament compress in which the filaments form between 3% and 30% of the total volume of the fibrous portion. However, this type of electrode still utilizes the same electrode surfaces for both pacing and sensing. The improved electrode according to one embodiment of the invention eliminates these problems by providing a large sensing area, a small pacing area, and a porous electrode tip which provides passive fixation to the endocardium.

DISCLOSURE OF INVENTION

The invention provides a tissue stimulation lead of the type having an electrode tip and an elongated electrical conductor encased in an encasing material which is generally inert to body fluids, the lead having an improved electrode tip including body means formed of an electrically-conductive material, a bundle of electrically-conductive fibers wherein the fibers are sufficiently compressed to form a fiber compress in which the fibers form at least 85 percent of the volume of the fiber compress, a first means for attaching the electrical conductive fibers to the body means, and a second means for attaching the electrically-conductive fibers to the body means.

In a specific embodiment of the invention, the body means is longitudinally extending, and forms a cavity at each end, one end being adapted to receive the electrical conductor, and the other end being adapted to receive the bundle of electrically-conductive fibers. Crimp means are used to attach both the electrical conductor and the bundle of carbon fibers to the body means. The fibers are aligned so that the axis of each fiber is substantially coplanar with the axes of the other fibers and the axis of the longitudinally extending body means. In a further embodiment of the invention, a sheath of nonconductive material is provided over most of the body means leaving only the rim exposed that forms the cavity in which the bundle of electrical conductive fibers is contained. In a further embodiment of the invention, the bundle of fibers is contained in a cylindrical sleeve which is positionable in the bundle-containing cavity. In a still further embodiment of the invention, an electrode tip is provided which has only the carbon fiber portion exposed to the heart. This electrode tip provides both improved sensing of heart activity through the carbon fibers and passive fixation to the heart endocardium.

BRIEF DESCRIPTION OF DRAWINGS

FIG. 1 is a view of a lead and associated electrode tip according to the invention;

FIG. 2 is a cross-sectional view taken along line 2—2 of FIG. 1;

FIG. 3 is a front view of the electrode tip taken along line 3—3 of FIG. 2;

FIG. 4 is a side view of a further embodiment of an electrode tip according to the invention;

FIG. 5 is a cross-sectional view taken along line 5—5 of FIG. 4;

FIG. 6 is a cross-sectional view of a further embodiment of an electrode tip according to the invention; and FIG. 7 is a still further embodiment of an electrode tip according to the invention.

BEST MODE FOR CARRYING OUT THE INVENTION

Detailed illustrative embodiments of the invention disclosed herein exemplify the invention and are considered to be the best embodiments for such purposes. They are provided by way of illustration and not limitation of the invention. Various modifications thereof will occur to those skilled in the art, and such modifications are within the scope of the claims which define the present invention.

As previously explained, an improved electrode tip is disclosed that includes a longitudinally extending, electrically-conductive body which forms cylindrical cavities at each end. One cavity receives the end of an elongated electrical conductor which connects the electrode tip to an implanted pulse generator such as a cardiac pacemaker. A plurality of electrically-conductive filars or fibers are compressed such that they form a bundle which is then inserted into the other cavity and attached therein. The fibers are sufficiently compressed so that they form at least 85 percent of the volume of the fiber compress. A nonconductive encasing material formed of a material that is generally inert to body fluids covers the elongated electrical conductor and at least a portion of the electrode tip. In some of the embodiments, a portion of the electrode tip is left exposed to the user's heart, the exposed portion enhancing the pacing characteristics of the lead, whereas the exposed electrical fibers are used for sensing electrical signals within the heart. Other embodiments disclosed include forming the fiber bundle so that a bullet-shaped protrusion of fibers extends outward from the cavity formed by the body means. These fibers may in turn be covered by a wire mesh to enhance interaction with heart tissue and thus provide a more positive fixation means for the electrode tip.

Referring now to FIG. 1, a lead 14 is shown having an electrode tip 16 at its distal end, and an elongated conductor 18 exposed at its proximal end. The exposed conductor 18 end is adapted to make electrical contact with an external or implanted tissue stimulating device (not shown) such as a heart pacemaker. The exposed end of the conductor 18 is in electrical contact with an exposed portion 20 of the electrode tip 16. Although a unipolar lead has been chosen for illustrative purposes, other types of leads, such as a bipolar lead, can be utilized with the improved electrode tip taught by the invention.

The electrode tip 16 of FIG. 1 is shown in cross-sectional view in FIG. 2. It includes a body portion 24 formed of an electrically-conductive, body-compatible material such as platinum. The body portion 24 is cylindrically-shaped, and forms first and second cylindrical cavities, 26 and 28, respectively, at each of its ends. The first cylindrical cavity 26 is adapted to receive the distal end of the conductor 18, and the second cylindrical cavity 28 is chosen to receive a bundle of electrical conductive fibers 30 to be explained in further detail below. The body portion 24 defining the second cylindrical cavity 28 forms an exposed annular lip 32 which extends around the perimeter of the cavity 28. A sheath 34 formed of a nonconductive, body-compatible material is utilized to encase the conductor 18 and the portion of the electrode tip 16 not intended to be in electrical contact with the user's body. Thus, the only portion of the electrode tip 16 in contact with the user's body is the exposed portion 44 of the bundle of electrically-conductive filars 30 and the annular lip 32 of the body portion 34. FIG. 3 is an end view of the electrode tip of FIG. 2 which shows the ends of the bundle of electrically-conductive fibers 30 and the annular lip 32. Referring again to FIG. 2, the conductor 18 is attached to the body portion 26 by a first annular crimp 36. In the specific embodiment shown, a cylindrically shaped retaining tube or sleeve 42, which is formed of a conductive material such as carbon, stainless steel or platinum, is utilized to hold the carbon fibers 30. However, it is not necessary that the retaining tube 42 be utilized. The retaining tube 42 and its associated fiber bundle 30, is attached to the body portion 24 by a second annular crimp 38.

In the specific embodiment shown in FIG. 2, the diameter $D_1$ of the carbon fibers bundle 30 is chosen to be approximately 0.030 inches, the outer diameter $D_2$ of the retaining tube 42 is chosen to be 0.040 inches, the diameter $D_3$ of the body portion 24 exclusive of the annular lip 32 is chosen to be 0.060 inches, and the length $L_1$ of fiber bundle 30 is chosen to be 0.125 inches. As previously explained, the carbon fibers are chosen to have a relatively small cross-sectional area and are pressed together to form the bundle 30. The fibers are sufficiently compressed to form a fiber compress in which the fibers form at least 85 percent of the volume of the fiber compress. The number of carbon fibers can vary depending on their cross-sectional areas. It has been found that a carbon fiber having less than a 15 micrometer diameter is desirable. Electrode tips utilizing 7 micrometer diameter fibers have been successfully tested. The compressed carbon fibers making up the bundle 30 are inserted into the retaining tube 42. The carbon fiber bundle 30 can be electroplated with a suitable material such as platinum to provide additional bonding of the fibers, while still providing a porous structure for passive electrode tip fixation in the heart.

In operation, this electrode tip provides advantages hitherto unobtained with prior art electrode tips. The annular lip 32 provides a higher current density for pacing with less overall energy expended. The carbon fiber bundle 30 exposes a large surface area for sensing and also provides passive electrode tip fixation through tissue ingrowth into the small cavities defined by the individual carbon fibers.

A further embodiment of an electrode tip utilizing carbon fibers according to the invention is shown in FIG. 4 and its crosssectional view is shown in FIG. 5. Here, a body portion 54 which is cylindrically shaped, as in the body portion 24 of FIG. 2, defines a first cavity 56 at its proximal end and a second cavity 58 at its distal end. The first cavity 26 diameter is chosen to slidably receive a conductor 60, the conductor 60 being secured to the body portion 54 by an annular crimp 62. A bundle of electrically-conductive filars or fibers 66 is provided, the end of the bundle being bullet-shaped and extending beyond the end of the second cavity 58. Each fiber in the bundle 66, as well as in the first bundle 30, is oriented so that its longitudinal axis is substantially coplanar with the longitudinal axes of the other fibers in the bundle. Substantially, as used herein, means that an attempt is made to longitudinally orient each fiber. Of course as a practical matter, the axis of each fiber will deviate slightly from the axes of the other fibers. The density of the fiber compress and the diameter of each fiber are the same as discussed in conjunction with FIG. 2. A platinum retaining mesh 68 is located over the tip of the bundle 66 and extends along the entire longitudinal length of the bundle as shown in FIG. 5, although, the retaining mesh 68 is not necessary to the teachings of the invention. It is not necessary that the retaining mesh 68 extend the entire length of the bundle 66, and it could extend only a nominal amount into the second cavity 56. The bundle 66 is attached to the body portion by a second annular crimp 70. The retaining mesh can be made from other conductive materials such as carbon, graphite, elgiloy, MP35N, or any of a number of other body-compatible materials. Further, the bundle of carbon fibers 66 can be electroplated with platinum to bond many of the fibers together while still providing a porous structure for passive tip fixation in the heart. This electroplating can be accomplished by various methods which are familiar to those skilled in the electroplating art. One such method utilizes a solution of conducting salts and platinum granules (i.e., a standard plating solution) and the electrode tip of FIG. 1 as the cathode. A platinum bar is used as the anode, the cathode and anode being set in the plating solution.

The amount of plating material deposited on the fibers is related to a voltage differential applied across the anode and cathode, and the length of time the electrode or cathode is allowed to stay in the bath. A voltage differential of six volts, for example, could be utilized. A satisfactory thickness for the platinum coat in this application has been found to be approximately 0.0001 thousands of an inch. This can be obtained by applying a 6 volt differential across the anode and cathode for approximately 30 seconds. Thus, flexure characteristics of the bullet-shaped electrode tip can be varied in accordance with the amount of electroplating applied to the fibers. If only a small amount of electroplating is utilized, a soft electrode tip is obtained which is desirable for some applications. Further, the porous structure remaining after the electroplating is sufficient to allow a slight ingrowth of tissue for passive electrode tip fixation.

FIG. 6 shows another embodiment of the lip 32 shown in FIG. 2. Referring to FIG. 6, a lip 74 defining the perimeter of the cavity 28' is curled to form an annular tube. Other portions of the electrode are as shown, such as the sheath 34', the retaining tube 42', and the bundle of electrically-conductive fibers 30'.

Referring now to FIG. 7, a further embodiment of the improved electrode tip is shown. Portions of the electrode tip include the body portion 76, the bundle of electrically-conductive fibers 78, the annular lip 80, and the retaining tube 82. The longitudinal axis of each fiber in the bundle 78 is oriented so that it is substantially coplanar with the longitudinal axes of the other fibers. However, these axes form an angle A with respect to the longitudinal axis of the body portion 76. Although A is shown as an acute angle, it could be any angle. Thus, the orientation of the passive fixation cavities formed by the filars can be varied in accordance with the angle A that is chosen, this orientation affecting the passive fixation and sensing characteristics of the electrode tip.

As can be readily appreciated, all of the electrode tips disclosed utilize a bundle of electrically-conductive fibers which provide a large sensing surface and a means for passive fixation of the electrode tip to the interior of the user's heart. Further embodiments of the electrode tip utilize a portion of the electrode body holding the bundle of fibers for pacing the heart, thereby allowing a higher current density with less energy being expended. In all of the embodiments described above, the longitudinal axes of the electrically-conductive fibers are oriented so that each is substantially coplanar with the other axes of the remaining fibers. It should be understood, however, that such is not necessary to be within the teachings of the invention, and that the fibers in the fiber compress could have any orientation with respect to each other. The configuration wherein the longitudinal axis of each fiber is substantially coplanar with the longitudinal axes of the other fibers was chosen primarily for use in obtaining the 85 percent or greater fiber density in the fiber compress.

What is claimed is:

1. In a tissue stimulation lead of the type having an electrode tip electrically connected to a distal end of an elongated electrical conductor encased in a nonconductive encasing material which is generally inert to body fluids, an improved electrode tip comprising:
   a body formed of an electrically-conductive material;
   a plurality of electrically-conductive fibers, each having a length less than said body, aligned so that the longitudinal axis of each fiber is substantially coplanar with the longitudinal axis of the other fibers, said fibers being sufficiently compressed to form a fiber compress in which said fibers form at least 85 percent of the volume of said fiber compress;
   first means for electrically connecting and attaching said body to the distal end of elongated electrical conductor; and
   second means for electrically connecting and attaching said fiber compress to said body, an end of said fiber compress comprising an exposed portion of the improved electrode tip, said exposed portion providing a surface area of the electrode tip that enhances sensing electrical signals within the tissue into which the electrode tip is inserted, said exposed portion also providing a porous structure to enhance passive fixation of the tissue to the electrode tip.

2. The improved electrode tip of claim 1 wherein said body includes a cavity containing at least a portion of said fiber compress.

3. The improved electrode tip of claim 2 wherein said electrically-conductive fibers are formed in a bundle which is at least partially contained within said cavity.

4. The improved electrode tip of claim 3 wherein said cavity is longitudinally extending, and said bundle is oriented in said cavity so that the longitudinal axis of said fibers are substantially coplanar with the longitudinal axis of said cavity.

5. The improved electrode tip of claim 4 wherein said bundle of electrically-conductive fibers extends outwardly from said cavity to form a protrusion.

6. The improved electrode tip of claim 5 further comprising a retaining mesh covering said protrusion.

7. The improved electrode tip of claim 4 further comprising sleeve means for holding said bundle, said sleeve means being received in said cavity.

8. The improved electrode tip of claim 1 wherein at least a portion of said body is encased in a nonconductive material which is generally inert to body fluids.

9. The improved electrode tip of claim 1 wherein the diameter of each of said electrically-conductive fibers is less than 15 micrometers.

10. In a tissue stimulation lead of the type having an electrode tip electrically connected to an elongated electrical conductor encased in a nonconducting encasing material which is generally inert to body fluids, an improved electrode tip comprising:
   a body formed of an electrically-conductive material;
   a bundle of longitudinally extending electrically-conductive fibers, each having a length less than said body, wherein the fibers are sufficiently compressed to form a fiber compress in which said fibers form at least 85 percent of the volume of said fibers compress;
   sleeve means for receiving at least a portion of said bundle;
   first means for electrically-connecting and attaching said sleeve means to said body; and second means for electrically connecting and attaching said body to an end of electrical conductor so that said body and said bundle are in electrical contact with each other and with said electrical conductor, an end of said bundle comprising an exposed portion of the electrode tip that enhances sensing electrical signals within the tissue into which the electrode tip is inserted and that provides a porous structure that enhances passive fixation of tissue thereto.

11. The improved electrode tip of claim 10 wherein said body is encased in a nonconductive sheath.

12. The improved electrode tip of claim 10 wherein said body is only partially encased in a nonconductive sheath.

13. The improved electrode tip of claim 10 wherein said fibers are aligned so that the longitudinal axis of each fiber is substantially coplaner with the longitudinal axes of the other fibers.

14. The improved electrode tip of claim 10 wherein the diameter of each of said electrically-conductive fibers is less than 15 micrometers, and the length of said fibers is no greater than 0.125 inches.

15. In a tissue stimulation lead of the type having an electrode tip electrically connected to an elongated electrical conductor encased in a nonconductive encasing material which is generally inert to body fluids, an improved electrode tip comprising:
  a bundle of longitudinally extending, electrically-conductive fibers;
  a longitudinally extending electrically-conductive body forming a first cavity at one end receiving an end of said elongated electrical conductor, and a second cavity at its other end receiving at least a portion of said bundle of electrically-conductive fibers, said bundle of fibers having a length less than said body; first means for electrically connecting and attaching said elongated electrical conductor end positioned in said first cavity to said body; and second means for electrically connecting and attaching said at least a portion of said bundle of electrically-conductive fibers positioned in said second cavity to said body and having a portion of said bundle exposed for contacting of tissue.

16. The improved electrode tip of claim 15 wherein said fibers are sufficiently compressed to form a fiber compress in which said fibers form at least 85 percent of the volume of said fiber compress.

17. The improved electrode tip of claim 16 wherein the diameter of each of said electrically-conductive fibers is less than 15 micrometers and the length of said bundle is no greater than 0.125 inches.

18. The improved electrode tip of claim 15 further comprising insulating means formed of a nonconductive material generally inert to body fluids for covering all of said body adjacent to the ambient environment except for a lip portion defining said second cavity.

19. The improved electrode tip of claim 15 wherein said bundle of electrically-conductive fibers comprises a plurality of fibers having longitudinal axes which are substantially coplanar with each other and with the longitudinal axis of said body.

20. The improved electrode tip of claim 15 wherein said second means for electrically connecting and attaching comprises sleeve means for receiving said at least a portion of said bundle of electrically-conductive fibers, said sleeve means being positioned in said second cavity.

* * * * *